United States Patent
Lanz

(10) Patent No.: US 9,187,381 B1
(45) Date of Patent: Nov. 17, 2015

(54) COMPOSITION AND METHOD FOR FORMULATING A BIOFERTILIZER AND BIOPESTICIDE

(71) Applicant: Bio AG Corp, Boca Raton, FL (US)

(72) Inventor: Lourdes Lanz, Boca Raton, FL (US)

(73) Assignee: Bio AG Corp., Boca Raton, FL (US)

( * ) Notice: Subject to any disclaimer, the term of this patent is extended or adjusted under 35 U.S.C. 154(b) by 0 days.

(21) Appl. No.: 14/258,356

(22) Filed: Apr. 22, 2014

(51) Int. Cl.
*C05G 3/02* (2006.01)

(52) U.S. Cl.
CPC .......................................... *C05G 3/02* (2013.01)

(58) Field of Classification Search
IPC .................................. C05F 11/08; A01N 63/00
See application file for complete search history.

(56) References Cited

FOREIGN PATENT DOCUMENTS

WO      WO 2014043604 A1 *  3/2014  ............. A01N 63/00

OTHER PUBLICATIONS

Güneş et al., "Nutritional content analysis of plant growth-promoting rhizobacteria," European Journal of Soil Biology 60:88-97, published online on Nov. 21, 2013.*

* cited by examiner

*Primary Examiner* — Rosanne Kosson
(74) *Attorney, Agent, or Firm* — Christian Sanchelima; Jesus Sanchelima

(57) ABSTRACT

A composition based on three strains of microorganisms to promote plant growth and serve as a plant protection product to protect plants from damaging influences including plant disease, pests or insects. The composition is comprised of *Paenibacillus polymyxa* $M_{10}$, *Azospirillum canadense* $B_2$, and *Bacillus pumilus* $L_{13}$. A mineral mix is used to maintain the microorganism viable for a long time, maintaining high efficacy as a biopesticide and biofertilizer. The mineral mix combined with the fermented microorganisms is then further combined with a nutritional additive to enhance the biofertilizing and biopesticidal features of the composition. The resulting composition can be applied to plants in liquid form or to the soil in solid form.

3 Claims, 3 Drawing Sheets

COMPOSITION AND METHOD FOR FORMULATING A BIOFERTILIZER AND BIOPESTICIDE

BACKGROUND OF THE INVENTION

1. Field of the Invention

The present invention relates to a biofertilizer and biopesticide composition using microorganisms and a method for formulating and applying the composition.

2. Description of the Related Art

Several compositions for fertilizers have been designed in the past. None of them, however, include a composition that consists essentially of *Bacillus pumilus* strain $M_{10}$, *Azospirillum canadense* strain $B_2$, and *Paenibacillus polymyxa* strain $L_{13}$ to simultaneously act like a biopesticide.

Applicant believes that the closest reference corresponds to U.S. patent application No. US 20130096003 filed by Ana Isabel Fernández Martinez, et al. However, it differs from the present invention because it does not include a method to formulate the composition in both liquid and solid forms. Moreover, it does not include a mineral mix to give the composition a slow release feature and promote the viability of the compositions in nutritionally depleted soils. Further the Fernandez application does not teach of a nutritional solution to provide for a high efficacy as a biofertilizer and biopesticide.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a composition for a biofertilizer and a biopesticide.

It is another object of this invention to provide a biofertilizer composition that is capable of nitrogen fixing, producing phytohormones and siderophores, and eliminate the need for chemical-based fertilizers for certain types of plants.

It is still another object of the present invention to provide a biopesticide composition that is anti-bacterial, a fungicide, and a nematicide characteristics. The use of this composition as a bio-pesticide maintains the health of plants and crops.

It is still another object of the present invention to provide a method to create the pesticide and fertilizer composition described above viable for a long time, maintaining high efficacy as biopesticide and biofertilizer. This method does not generate any kind of wastes.

It is yet another object of the present invention to provide a method for producing the above composition and including a step of introducing a mineral mix.

It is yet another object of this invention to provide such a composition that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

The present invention includes a composition comprising of three strains of microorganisms, namely, *Bacillus pumilus* strain $M_{10}$, *Azospirillum canadense* strain $B_2$, and *Paenibacillus polymyxa* strain $L_{13}$.

The composition acts as a biofertilizer that is a solubilizer of phosphates and potassium. In addition, as a biofertilizer the composition is capable of nitrogen fixing, produces phytohormones, namely cytokinins and Gibberellin. It also produces siderophores and reduces and can potentially eliminate the need for chemical-based fertilizers. The phytohormones are used to stimulate the growth of vegetables and their roots.

Figure 1:
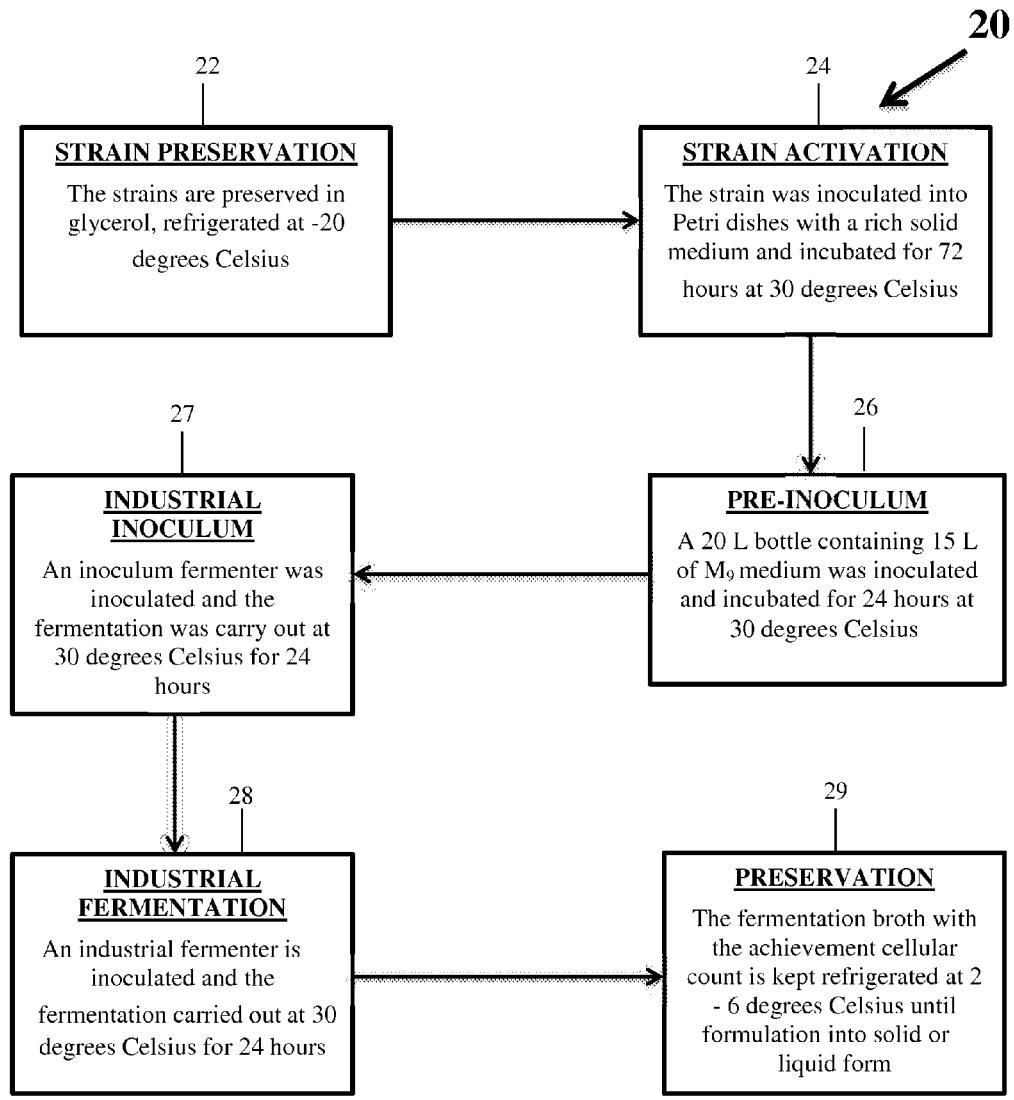
FIG. 1 represents a flow chart showing the steps involved in the fermentation process of each microorganism used in the composition.

As seen in FIG. 1, fermentation process 20 undergoes several steps. The fermentation process for each strain beings with conserving each strain in glycerol at $-20°$ C. until needed as shown in step 22. The fermentation process then undergoes several stages of inoculation to increase the cellular count of each strain in the composition. The first step in the inoculation is to activate the three strains. This is done in a Petri dish with an Agar solid medium and is incubated at 30 degrees Celsius for 72 hours as shown in step 24. The second step in the inoculation process is referred to as pre-inoculation, as shown in step 26, and is generally done in a laboratory. A working volume of the three strains is combined in sufficient nutritional solution, M9, so as to fill approximately 60-90% of a bioreactor vessel. The strains remain in the nutritional solution within the bioreactor vessel for 24 hours. The nutritional solution, M9, includes (quantities are per liter of water): 5 g of protein hydrolyzer, 5 g of soy flour, 1 g of yeasts extract, and 2 g of sodium chloride. Pre-inoculation step 26 is used to further reproduce the cellular count of each strain. The resulting product from pre-inoculation step 26 is used to inoculate an even larger bioreactor vessel that can further reproduce the cellular count of each strain, as shown in step 27. Step 27 is repeated using the same proportion and time requirements described above until the desired cellular count for each strain is achieved. In a preferred embodiment, step 27 is performed until the cellular count for each strain is at least $10^9$ UFC×$mL^{-1}$ for each strain. The bioreactor vessel that ends up with the desired cellular count is known as the industrial fermenter as shown in step 28. The fermentation broth with the desired cellular count obtained in step 28 is then kept refrigerated at 2-6 degrees Celsius until formulation into solid or liquid form. The cultures should not be maintained for longer than 30 days. The same process is repeated for the microorganism strain, *Paenibacillus polymyxa* $L_{13}$ and *Azospirillum canadense* $B_2$. The *Azospirillum canadense* $B_2$ strain ends up slightly less concentrated than the previous two strains and also ends up with a slightly elevated pH.

Figure 2:
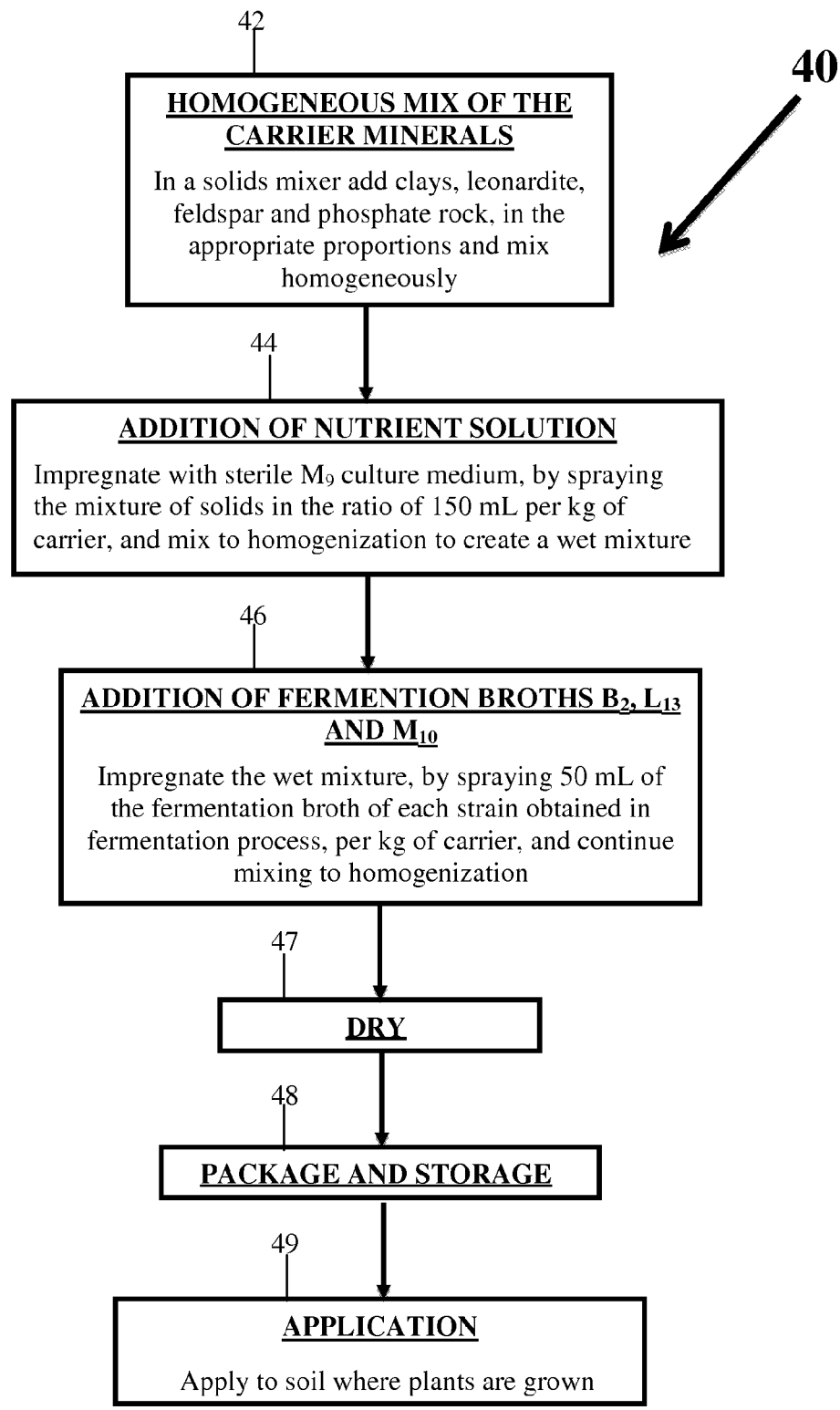
FIG. 2 represents a flow chart illustrating the steps involved in the method used to produce an embodiment of the present invention in solid form.

The composition can be formulated in liquid or solid form, however, in both cases the composition is made up of each microorganism in equal parts. As seen in FIG. 2, to produce the composition in solid form 40 each microorganism undergoes fermentation process 20 so that each microorganism can reproduce. A mineral mix, as shown in step 42, is used when formulating the composition in solid form to maintain the microorganisms viable, stimulate reproduction and promote a slow release of the composition. The mineral mix, which has a slow release function, includes in a preferred embodiment, 5% leornadite, 2% feldspar, 2% phosphate rock, and 91% clay by weight.

The mineral mix provides a minimum of basic nutrients to plants and crops. It also has a slow release function and preserves the viability of the microorganisms during the time between manufacturing and application. The purpose of the leornadite as organic matter is to provide nutrition to plants. The purpose of the feldspar is provide a source of potassium in case the soil does not have sufficient potassium to allow plant growth. The purpose of the phosphate rock is to provide a source of phosphate in case the soil does not have sufficient phosphate to stimulate plant growth. The purpose of the clay is to release cells slowly. Once the cells are released they begin to solubilize potassium from the feldspar and phosphate from the phosphate rock. In addition to potassium and phosphate, plants require nitrogen, which is fixed in the composition using the three microorganisms that make up the composition. The granular size of each mineral is preferably not to exceed approximately 1.5 mm. However, is has been found that a range for this diameter could be from 0.5 mm to 2.5 mm.

The minerals are all mixed to create a homogenous mix that is used as a carrier for the absorption of the microorganisms. As seen in step 44 the homogenous mix is then impregnated with a nutritional solution, also referred to as M9, in the proportion of 150 mL of nutritional solution, M9, per 1 kg of mineral mix, also known as a carrier, to create a wet mixture. The wet mixture previously obtained is then impregnated with 50 mL of the fermentation broth of each strain, as seen in step 46. The resulting product is then dried at no more than 45 degrees Celsius until the moisture level is no higher than 10%, as shown in step 47. The resulting product is then packaged and stored as seen in step 49. Finally, the resulting composition in solid form is applied to the soil where the plants are grown.

Figure 3:
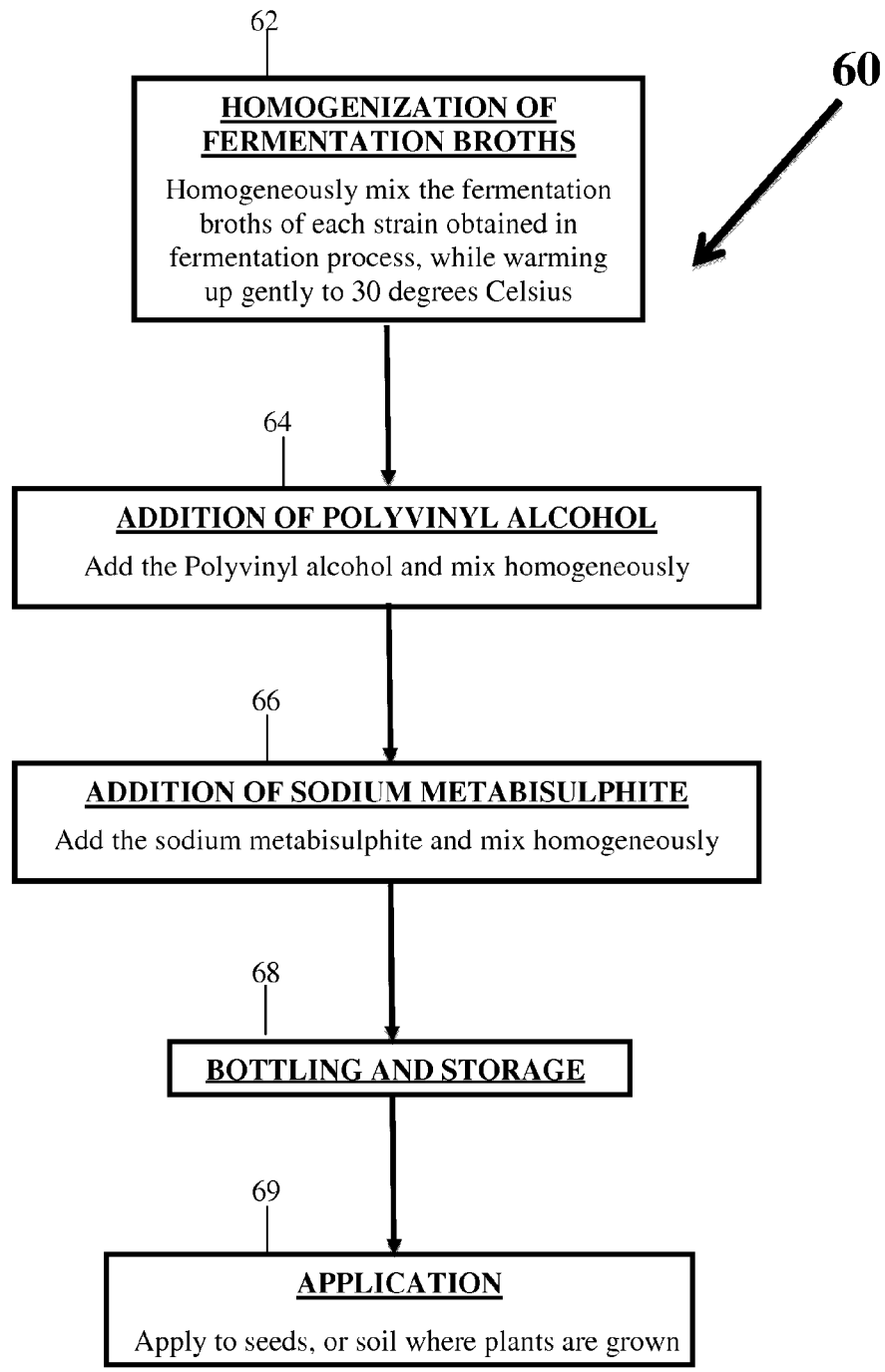
FIG. 3 shows a flow chart illustrating the steps involved in the method used to produce an embodiment of the present invention in liquid form.

As seen in FIG. 3, the method to apply the composition in liquid form 60 consists of undergoing the three fermentations done using fermentation process 20, one for each microorganism so that each microorganism can reproduce. The fermentation process is the same for liquid form as it is for solid form. The fermented broth with microorganisms is then homogenously mixed, as shown in step 62, with polyvinyl alcohol as shown in step 64, and sodium metabisulfite, as shown in step 66, to create a homogenous mix using the following proportions, in a preferred embodiment:
 a) 315 mL of *Paenibacillus polymyxa* $L_{13}$ culture;
 b) 315 mL of *Azospirillum canadense* $B_2$ culture;
 c) 315 mL of *Bacillus pumilus* $M_{10}$ culture;
 d) 50 mL of polyvinyl alcohol; and
 e) 0.15 g of sodium metabisulfite The final product in liquid form is then bottled and stored as shown in step 68 and added to seeds or the soil where plants are grown, as shown in step 69.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method for fermenting a composition comprising strains of *Paenibacillus polymyxa, Azospirillum canadense*, and *Bacillus pumilus*, comprising the steps of:
 a) isolating three strains of microorganisms, said microorganisms being *Paenibacillus polymyxa* $L_{13}$, *Azospirillum canadense* $B_2$, and *Bacillus pumilus* $M_{10}$,
 b) conserving each strain in glycerol at $-20°$ C. until needed,
 c) inoculating each said strain in a Petri dish with an Agar solid medium and at 30 degrees Celsius for 72 hours,
 d) creating a culture by filling 60-90% of a bioreactor vessel with a combination of the three microorganisms of step (a) in equal parts and a nutritional solution,
 e) incubating said culture at 30 degrees Celsius for 24 hours,
 f) creating an industrial fermentation broth by inoculating increasingly larger bioreactor vessels to further reproduce the cellular count of each said strain, maintaining said 60-90% proportion of filling the bioreactor vessels, until the desired said cellular count for each said strain is achieved, and
 g) keeping said fermentation broth refrigerated at 2-6 degrees Celsius until needed.

2. The method for fermenting said microorganisms set forth in claim 1 wherein said desired cellular count for each said strain is $10^9$ UFC×$mL^{-1}$.

3. The method for fermenting said microorganisms set forth in claim 1 wherein said nutritional solution includes 5 g of protein hydrolyzer, 5 g of soy flour, 1 g of yeast extract, and 2 g of sodium chloride, per liter of water.

* * * * *